US009933349B2

(12) United States Patent
Vacca et al.

(10) Patent No.: US 9,933,349 B2
(45) Date of Patent: *Apr. 3, 2018

(54) METHOD FOR DETERMINING VOLUME AND HEMOGLOBIN CONTENT OF INDIVIDUAL RED BLOOD CELLS

(71) Applicant: Abbott Laboratories, Abbott Park, IL (US)

(72) Inventors: Giacomo Vacca, San Jose, CA (US); Martin Krockenberger, Los Gatos, CA (US); Diana Garrett, Scotts Valley, CA (US)

(73) Assignee: Abbott Laboratories, Abbott Park, IL (US)

( * ) Notice: Subject to any disclaimer, the term of this patent is extended or adjusted under 35 U.S.C. 154(b) by 114 days.

This patent is subject to a terminal disclaimer.

(21) Appl. No.: 15/044,635

(22) Filed: Feb. 16, 2016

(65) Prior Publication Data

US 2016/0258853 A1 Sep. 8, 2016

Related U.S. Application Data

(63) Continuation of application No. 14/562,058, filed on Dec. 5, 2014, now Pat. No. 9,261,515, which is a continuation of application No. 12/657,218, filed on Jan. 15, 2010, now Pat. No. 8,906,308.

(51) Int. Cl.
*G01N 15/06* (2006.01)
*G01N 33/49* (2006.01)
*G01N 15/14* (2006.01)
*G01N 33/72* (2006.01)
*G01N 15/00* (2006.01)

(52) U.S. Cl.
CPC ......... *G01N 15/06* (2013.01); *G01N 15/0656* (2013.01); *G01N 15/147* (2013.01); *G01N 15/1459* (2013.01); *G01N 33/492* (2013.01); *G01N 33/4915* (2013.01); *G01N 33/721* (2013.01); *G01N 2015/0065* (2013.01); *G01N 2015/0073* (2013.01); *G01N 2015/0687* (2013.01); *G01N 2015/0693* (2013.01); *G01N 2333/805* (2013.01); *Y10T 436/101666* (2015.01)

(58) Field of Classification Search
CPC ........... G01N 15/1459; G01N 15/1434; G01N 15/0205; G01N 15/0227; G01N 15/1463; G01N 15/06; G01N 15/0656; G01N 15/147; G01N 1/38; G01N 2015/1486; G01N 2015/025; G01N 2015/1452; G01N 2015/1493; G01N 2015/0065; G01N 2015/0073; G01N 2015/0693; G01N 2015/0687; G01N 33/721; G01N 33/4915; G01N 33/492; G01N 2333/805
See application file for complete search history.

(56) References Cited

U.S. PATENT DOCUMENTS

| | | |
|---|---|---|
| 2,656,508 A | 10/1953 | Coulter |
| 3,810,011 A | 5/1974 | Coulter et al. |
| 4,284,355 A | 8/1981 | Hansen et al. |
| 4,521,518 A | 6/1985 | Carter et al. |
| 4,528,274 A | 7/1985 | Carter et al. |
| 4,735,504 A | 4/1988 | Tycko |
| 5,017,497 A | 5/1991 | Gerard de Grooth et al. |
| 5,125,737 A | 6/1992 | Rodriguez et al. |
| 5,194,909 A | 3/1993 | Tycko |
| 5,266,269 A | 11/1993 | Niiyama et al. |
| 5,284,771 A | 2/1994 | Fan et al. |
| 5,350,695 A | 9/1994 | Colella et al. |
| 5,360,739 A | 11/1994 | Fan et al. |
| 5,378,633 A | 1/1995 | Von Behrens et al. |
| 5,438,003 A | 8/1995 | Colella et al. |
| 5,631,165 A | 5/1997 | Chupp et al. |
| 5,763,280 A | 6/1998 | Li et al. |
| 5,834,315 A | 11/1998 | Riesgo et al. |
| 5,882,934 A | 3/1999 | Li et al. |
| 5,935,857 A | 8/1999 | Riesgo et al. |
| 5,939,326 A | 8/1999 | Chupp et al. |
| 6,025,201 A | 2/2000 | Zelmanovic et al. |
| 6,114,173 A | 9/2000 | Zelmanovic et al. |
| 6,524,858 B1 | 2/2003 | Zelmanovic et al. |
| 6,573,102 B2 | 6/2003 | Li et al. |
| 6,623,972 B2 | 9/2003 | Malin et al. |
| 6,706,526 B2 | 3/2004 | Lang et al. |
| 7,361,512 B2 | 4/2008 | Qian et al. |
| 7,397,232 B2 | 7/2008 | Hu et al. |

(Continued)

FOREIGN PATENT DOCUMENTS

WO     WO 02099380     12/2002

OTHER PUBLICATIONS

Huisman et al. "A feasability study of simultaneous optical/fluorescence erythrocyte analysis using the Abbott CELL-DYN Sapphire." Abstracts of the XXist International Symposium on Technological Innovations in Laboratory Hematology (2008) 119 pp. 66-67.

(Continued)

*Primary Examiner* — Christopher A Hixson
(74) *Attorney, Agent, or Firm* — Edward J. Baba; Bozicevic, Field & Francis LLP

(57) ABSTRACT

Provided herein is a method for determining the volume or hemoglobin content of an individual red blood cell in a sample containing a population of red blood cells. The method may be performed on a hematology analyzer. Also provided are a hematology analyzer for performing the method and a computer-readable medium containing programming for performing the method.

20 Claims, 13 Drawing Sheets

(56) References Cited

U.S. PATENT DOCUMENTS

| | | |
|---|---|---|
| 2003/0025896 A1 | 2/2003 | Oever et al. |
| 2005/0219527 A1 | 10/2005 | Ikeuchi et al. |
| 2008/0153170 A1 | 6/2008 | Garrett et al. |
| 2008/0158561 A1 | 7/2008 | Vacca et al. |
| 2008/0268494 A1 | 10/2008 | Linssen |

OTHER PUBLICATIONS

Van Hove et al. (2000) "Anemia Diagnosis, Classification, and Monitoring Using Cell-Dyn Technology Reviewed for the New Millennium" *Laboratory Hematology* 6:93-108.

METHOD FOR DETERMINING VOLUME AND HEMOGLOBIN CONTENT OF INDIVIDUAL RED BLOOD CELLS

BACKGROUND OF THE INVENTION

Variations in the morphological and physiological characteristics of red blood cells in a patient's blood provide valuable information concerning the pathological condition of many specific types of red cell disorders or anemias. In diagnosing such disorders, the mean cellular hemoglobin concentration (MCHC) and the mean cell volume (MCV) may be measured to provide valuable insight into the condition of a patient. Such information may be used in conjunction with the microscopic evaluation of the distribution of sizes, shapes and color of red cells in a stained blood smear by a trained hematologist and with other biochemical tests. Variations in the refractive index of individual red cells are highly correlated with their hemoglobin concentration, and this information can be combined with size measurements to provide diagnostic value. For example, in microcytic anemias, the size of the red cells and, therefore, also the MCV are significantly reduced, but the optical density (related to the refractive index) and the MCHC are somewhat elevated. In megaloblastic anemias, both the size (macrocytes) and the MCHC are somewhat increased.

This disclosure relates in part to a method for determining the volume and/or hemoglobin content of individual red blood cells using a hematology analyzer, and a hematology analyzer for performing the method.

SUMMARY OF THE INVENTION

Provided herein is a method for determining the volume or hemoglobin content of an individual red blood cell of a blood sample using a hematology analyzer, and a hematology analyzer for performing the method. In general terms, the method involves obtaining a set of data points for a sample comprising a population of red blood cells using a hematology analyzer; and calculating the volume or hemoglobin content of an individual red blood cell in said sample containing using: (I) measurements of individual red blood cells in a plurality of a optical scattering channels (e.g., axial light loss, intermediate angle scattering, and/or polarized side scattering channels, etc.); (II) the mean cell volume of the population of red blood cells calculated using measurements from a separate impedance transducer, (III) the bulk hemoglobin concentration of the sample measured on a separate colorimetric transducer; (IV) the number of cells in the population of red blood cells; (V) the mean values of the measurements of the population of red blood cells on the plurality of said optical scattering channels; and (VI) the median-of-means value of prior populations of red blood cells analyzed on at least one of said optical scattering channels on said hematology analyzer. Computer-related embodiments are also provided.

DETAILED DESCRIPTION

Figure 1:
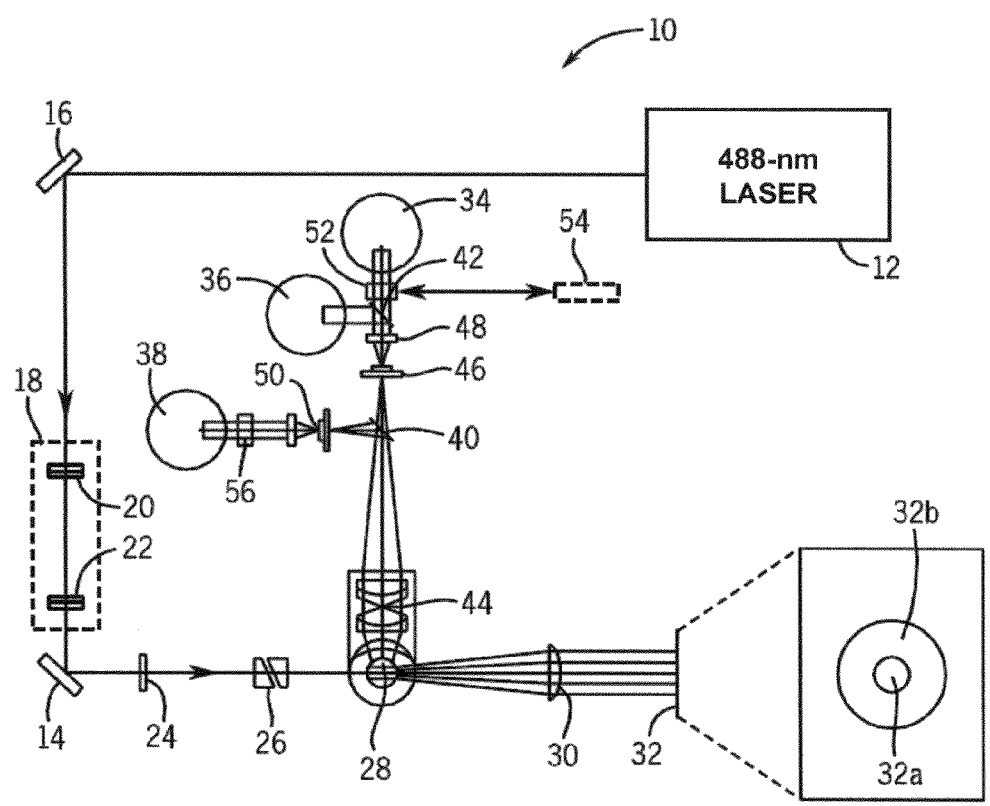
FIG. 1 is a schematic illustration of the optical subassembly of an exemplary hematology analyzer.

Before the present invention is described in detail, it is to be understood that this invention is not limited to particular variations set forth and may, of course, vary. Various changes may be made to the invention described and equivalents may be substituted without departing from the true spirit and scope of the invention. In addition, many modifications can be made to adapt a particular situation, material, composition of matter, process, process act(s) or step(s), to the objective(s), spirit or scope of the present invention. All such modifications are intended to be within the scope of the claims made herein.

Steps of any method recited herein can be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described can be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. For example, if a value is compared to "a criterion", the value may be compared to one or more criteria, i.e., a single criterion or multiple criteria. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The following abbreviations may be used in this disclosure: CBC (complete blood count), RBC (red blood cell or erythrocyte), rRBC (lysis-resistant red blood cell or erythrocyte), Retic (reticulocyte, an immature red blood cell), HGB (hemoglobin), MCHC (mean corpuscular, or cell, hemoglobin concentration), MCV (mean corpuscular, or cell, volume), RDW (red blood cell distribution width), PLT (platelet), WBC (white blood cell or leukocyte), fWBC (fragile white blood cell or leukocyte), NEU (neutrophils), LYM (lymphocytes), MON (monocytes), DSS (depolarized side scatter), CLL (chronic lymphocytic leukemia), ALL (axial light loss), IAS (intermediate angle scatter), PSS (polarized side scatter), DSS (depolarized side scatter), and FCS (flow cytometry standard). Generally, uppercase acronyms are used to indicate a measurement method, assay, or detection channel (e.g., HGB, IAS), while lowercase italics are used to indicate values obtained from such measurements (e.g., mcv, pss). In addition, the term "cell" may be used to refer to any of the formed bodies commonly or pathologically found in peripheral blood, e.g., RBCs and WBCs, and also including PLTs. Other abbreviations may be defined below.

In this disclosure, the term "FCS file" is used to describe a digital representation of the collection of detected events captured by the analyzer and classified (as, e.g., RBCs, lymphocytes, etc.) by automated internal algorithms. The events in the FCS file may also be referred to as "list mode" data, reflecting one aspect of the FCS file format, in which events are arranged in a list ordered sequentially by time of detection.

Hematology Analyzers

As noted above, a hematology analyzer that provides the volume and/or the amount of hemoglobin of individual red blood cells of a sample is provided. In general terms, the hematology analyzer comprises: a) a flow cell; b) a light source for directing light to said flow cell; c) a plurality of detectors for detecting light scattering by cells on a plurality of optical scattering channels; d) an apparatus for measuring bulk hemoglobin concentration in a cell lysate; e) an impedance transducer for measuring changes in impedance attendant to the passage of individual cells; and f) a data analysis workstation comprising programming to calculate the volume or hemoglobin content of an individual red blood cell in a sample containing a population of red blood cells using: (I) measurements of said individual red blood cells on a plurality of said optical scattering channels; (II) the mean cell volume of said population of red blood cells calculated using impedance values; (III) the bulk hemoglobin concentration of said sample; (IV) the number of cells in said population of red blood cells; (V) the mean values of the measurements of said population of red blood cells on said plurality of said optical scattering channels; and (VI) the median-of-means value (i.e., the median of the means) of prior populations of red blood cells analyzed on at least one of said optical scattering channels on said hematology analyzer.

The methodology described below include several calculations that may be generally employed on any suitable flow cytometer in the form of programming, including a hematology analyzer, examples of which are known on the art and described in, e.g., U.S. Pat. Nos. 5,017,497, 5,266,269, 5,378,633, 5,631,165, and 6,524,858, as well as published U.S. Patent Applications US20080153170, US20080158561 and US20080268494, the disclosures of which are incorporated herein by reference in their entirety. Hematology analyzers analyze samples of whole blood to determine, among other results, the concentration of erythrocytes, platelets, and hemoglobin. The optical subassembly of an exemplary hematology analyzer is schematically illustrated in FIG. 1. One of skill in the art would recognize that the choice, number and design of the components (e.g., the type of laser used, the number and specifications of the optical components, etc.) can vary greatly between analyzers and, as such, the hematology analyzer of FIG. 1 is provided as an example and should not be used to limit this disclosure. For example, in certain cases a hematology analyzer may or may not detect fluorescence. In addition to the optical components shown in FIG. 1, a hematology analyzer may contain an impedance-measuring device for measuring changes in impedance as cells pass through (e.g., enter or exit) the flow cell. Such an apparatus includes an impedance meter, examples of which are described in U.S. Pat. Nos. 2,656, 508, 3,810,011 and 5,125,737, which are incorporated by reference herein in their entirety. Electrical impedance measurements may be used to count and size (e.g., calculate the volume of) cells passing through the flow cell.

Referring now to FIG. 1, exemplary hematology analyzer 10 comprises a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bull's-eye detector 32, a first photomultiplier tube 34, a second photomultiplier tube 36, and a third photomultiplier tube 38. The bull's-eye detector 32 has an inner detector 32a for measuring extinction of the forward-propagating beam (the data produced therefrom being referred to as "axial light loss" or "ALL") and an outer detector 32b for light scattering in an annulus of 3° to 10° from forward (otherwise referred to as "intermediate angle scatter" or "IAS"). The source of light 12 can be a vertically polarized 488-nm air-cooled argon-ion laser or a vertically polarized blue (488 nm) solid-state laser. Other laser wavelengths can be substituted, with attendant changes in the optical design layout (i.e., selection, positioning and characteristics of the optical components). Additional details relating to the laser, the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11.

The forward optical path system of the hematology analyzer shown in FIG. 1 includes a plano-convex lens 30 and a two-element photodiode detector 32 located in the back focal plane of the lens. In this configuration, each concentric ring within the outer photodiode detector 32b maps to a specific incremental angular collection annulus of light from cells moving through the flow cell 28. The detector 32 can be a bull's-eye detector capable of detecting axial light loss (ALL) and intermediate angle forward scatter (IAS). U.S. Pat. No. 5,631,165 describes various alternatives to this detector at column 43, lines 12-52.

The first photomultiplier tube 34 (PMT1) measures depolarized side scatter (DSS) or green fluorescence (FL1). The second photomultiplier tube 36 (PMT2) measures polarized side scatter (PSS) or yellow to orange fluorescence (FL2)

and the third photomultiplier tube 38 (PMT3) measures red fluorescence (FL3). FL1, green fluorescence, is detected between about 515 to 545 nm. FL2, yellow to orange fluorescence, is detected between about 565 to 595 nm. FL3, red fluorescence, is detected between about 615 to 645 nm. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens of condenser assembly 44 to the flow cell 28 by means of a refractive index-matching layer, enabling collection of light over a wide angle. U.S. Pat. No. 5,631,165 describes various additional details of this optical system at column 44, lines 5-31.

The condenser 44 is an optical lens system with aberration correction sufficient for diffraction-limited imaging used in high resolution microscopy. U.S. Pat. No. 5,631,165 describes various additional details of this optical system at column 44, lines 32-60.

The functions of other components shown in FIG. 1, i.e., a slit 46, a field lens 48, and a second slit 50, are described in U.S. Pat. No. 5,631,165, at column 44, line 63 through column 45, line 15. The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam). A slider assembly placed in front of photomultiplier 34 allows dual use of photomultiplier 34: to detect depolarized side scatter (DSS) when polarizer 52 is moved in the light path, and to detect green fluorescence (FL1) when filter 54 is moved in the light path. A similar slider assembly (not shown) placed in front of photomultiplier 36 allows the dual use of detecting polarized side scatter (PSS) and yellow-orange fluorescence (FL2). Photomultiplier 38 is configured with filter 56 to detect red fluorescence (FL3) only.

As would be readily apparent, numerous variations of the above-described analyzer are possible. For example, the two cylindrical lenses may be replaced by an anamorphic prism pair, the bull's-eye detector can be replaced by separate detectors and a holed mirror, and other wavelengths of light may be employed.

An example of a hematology analyzer that does not detect fluorescence is described in U.S. Pat. No. 5,378,633, particularly at col. 24, line 47 to col. 25, line 36 and FIGS. 6 and 7. This description is incorporated by reference herein.

A suspension of blood containing erythrocytes may be propelled from a sample nozzle where it comes into contact with a fast-moving, laminar-flow sheath stream. In a process known as hydrodynamic focusing, the sample stream is squeezed into a thin central core. This arrangement usually ensures that only a single cell is in the sensing region of the laser beam at any given time.

The measurement process begins as the cell core stream passes through the flow cell 28, having been diluted with the diluent so that the cells pass through the laser-illuminated volume substantially in single file, in a laminar flowing sample stream surrounded by a sheath fluid. The illuminated volume is bounded by the intersection of the laser beam and the sample stream, and in one embodiment it has the approximate dimensions of 80 µm along the laser propagation direction, 20 µm along the sample stream flow direction, and about 5-10 µm in a direction transversal to both sample flow and laser beam propagation.

Light scattered at 90 degrees to the axis of the laser beam may be collected using photomultipliers (PMTs). Photomultipliers, not photodiodes, are used in the 90-degree channels because relatively little light is scattered at high angles, and because they can also be used to detect the generally much lower-intensity fluorescence emissions. If the impinging polarized light undergoes optical scattering mainly from the cell membrane and nucleus (if present), it generally retains its original vertical plane of polarization. However, if it interacts with certain subcellular components that may be present in the cytoplasm, e.g., granules or anisotropic structures, then the scattered light can have an altered angle of polarization. In order to exploit this phenomenon, one of the PMTs may have a horizontal polarizer in front of it. This polarizer prevents vertically polarized light from striking the photomultiplier. Therefore, any light detected by the "90-degree depolarized" PMT is light that has been depolarized by its interaction with a cellular substructure—usually a leukocyte, and particularly a eosinophil. The second photomultiplier (the "90-degree polarized" PMT) may receive the scattered light reflected off a beam splitter that is angled at 45 degrees and designed to mostly reflect vertically polarized light and mostly transmit horizontally polarized light at the excitation (laser) wavelength. The major portion of the light detected by this second photomultiplier is vertically polarized side-scattered light and carries information correlated with the conformation of the nucleus. The scattering light detection scheme briefly summarized here is a proprietary design referred to as Multi-Angle Polarized Scattering Separation (MAPSS), and described in fuller detail in U.S. Pat. No. 5,017,497. This description is incorporated by reference herein.

Data obtained from the photosensors may be used to construct a multi-dimensional scattergram (comprising two to five or more dimensions, and typically four). Any three dimensions can be viewed using the computer graphics capabilities of the instrument which enable a three-dimensional "solid" representation to be rotated in space—color being used to identify the different classifications of cell populations effected by automated algorithms programmed on the data station, or alternately used to map the values from a fourth dimension. For purposes of paper documentation, the four-dimensional scattergram can be examined by six user-selectable pairs of two-dimensional scatter plots or projections and by numerous user-selectable one-dimensional histogram projections.

The data may be analyzed in order to enumerate, for example, the erythrocytes and platelets in the sample, as well as to enumerate, for example, the immature erythrocytes (e.g., reticulocytes) in the sample. Reticulocytes may be distinguished from mature erythrocytes by use of a nucleic-acid dye or stain in the reagent solution which, upon binding to the RNA contained in the immature cell (but absent from a mature one), so labels the reticulocyte to allow its identification by fluorescent or light-scattering means. The data may be further analyzed in accordance with methods described in greater detail below.

The bulk hemoglobin concentration (HGB) of a blood sample is measured on an automated hematology analyzer by mixing a separate aliquot of a blood sample with a lytic reagent, and measuring the hemoglobin concentration of the resultant cell lysate using a colorimetric transducer. Upon exposing to the lytic reagent, the red blood cells are completely lysed, and hemoglobin is released to the sample mixture, which upon reacting with a ligand in the lytic reagent forms a chromogen. The hemoglobin chromogen is then measured by colorimetry at a predetermined wavelength, and HGB is calculated from the measurement. One lysing reagent system suitable for measuring HGB comprises an isotonic blood diluent, such as the diluents described in U.S. Pat. Nos. 4,521,518, 4,528,274, 5,935,857 and 6,706,526, and a lysing reagent, such as the lysing reagents described in U.S. Pat. Nos. 5,763,280, 5,834,315 and 6,573,102; these are hereby incorporated by reference in their entirety. Alternatively, the reagent system can also be a single lysing reagent as described in U.S. Pat. No. 5,882,934 which is hereby incorporated by reference in its entirety. Furthermore, various lytic reagents known in the art for measurement of hemoglobin can be used for the purpose of the present invention.

Impedance may be measured using a non-focused flow aperture, and the blood sample can be highly diluted, for example with a dilution ratio of 6250:1. When a focused flow cell is used for the measurement, the dilution ratio can be substantially lower, such as 290:1. To maintain the volume and morphology of the red blood cells during their measurements on a hematology analyzer, an isotonic diluent is used for diluting the blood sample. Typically, the diluent contains one or more alkaline metal salts. Various commercially available isotonic blood diluents can be used for diluting the blood sample. Suitable examples include, but are not limited to, the diluents described in U.S. Pat. Nos. 4,521,518, 4,528,274, 5,935,857 and 6,706,526. When a particle or a blood cell, suspended in a conductive solution, passes through an aperture, an electrical signal, or a pulse, can be measured due to the increase of impedance. The electrical pulses can be used for counting the number of blood cells of a blood sample. Also, the pulse shape, height and width are directly related to the volume or size of a particle, and can be converted to the volume of the cell measured. When a sample that contains two or more different blood cells having different volumes is measured, a histogram obtained from the measurement can represent the volume distribution of these blood cells. The detection methods and apparatus used for blood cell counting and sizing by a blood analyzer equipped with an impedance meter are generally described in U.S. Pat. Nos. 2,656,508, 3,810,011 and 5,125,737, which are hereby incorporated by reference in their entirety.

Methodology

In the discussion that follows below and in the Examples section, certain calculations may be described using the phrase "inputting measurements into a formula" or a grammatical equivalent thereof. As would be recognized, any single calculation may be performed as a multi-step method, and many multi-step calculations can be described using a single formula. As such, any method that has a step that "inputting measurements into a formula" or the like is not intended to be limited to only those embodiments that involve inputting measurements into a single formula. As would be recognized and as illustrated in the Examples section herein, such a calculation may be done using a number of different steps, each using a different formula, that lead to the same result as if a single formula were employed. All methods, including those that employ different measurement units and different formulae that lead to the same results similar to or the same as those described below are contemplated herein. All steps of the calculating method may be performed using a computer, and the various steps of the calculation may be embodied on a computer-readable medium in the form of programming. Further, in several embodiments described below, the method may be described as a method of calculating the volume or hemoglobin content of an individual red blood cell in a sample "using" multiple variables. As would be understood, the term "using" includes inputting the variables, or a derivative thereof, into a formula that, when executed, outputs a result, i.e., the volume or hemoglobin content of an individual red blood cell in a sample. The terms "algorithm" and "formula" are used synonymously and, as noted above, are not intended to imply that any calculation can be solved using a single step.

In certain embodiments, certain metrics of a red blood cell population (e.g., the number of cells in the population, the mean cellular hemoglobin concentration of the population, the mean cell volume, etc.) may be calculated without using optical scattering measurements, e.g., calculated using impedance and bulk hemoglobin measurements. Such methods are known in the art, and are described in detail in references cited above.

Provided herein is a method of sample analysis. In general terms, the method comprises obtaining a set of data points for a sample comprising a population of red blood cells using a hematology analyzer; and calculating the volume or hemoglobin content of an individual red blood cell in the sample containing using: (I) measurements of individual red blood cells on a plurality of a optical scattering channels; (II) the mean cell volume of the population of red blood cells calculated using impedance values; (III) the bulk hemoglobin concentration of the sample; (IV) the number of cells in the population of red blood cells; (V) the mean values of the measurements of the population of red blood cells on the plurality of the optical scattering channels; and (VI) the median-of-means value of prior populations of red blood cells analyzed on at least one of the optical scattering channels on the hematology analyzer. In certain embodiments and as will be described below the measurements of whichever optical scattering channels are used may be filtered to remove data points generated by noise and coincidences prior to use. Also as will be described below, the measurements may be scaled (i.e., multiplied by a suitable factor in order to minimize differences between analyzers and the effect of drift on any one analyzer) and normalized (i.e., mathematically transformed to yield quantities centered around 0 and generally distributed between −1 and 1) as part of the method.

In certain embodiments and as described in greater detail in the Examples section of this disclosure, the volume of individual red blood cells in the sample may be calculated using: (I) measurements of individual red blood cells on ALL and IAS channels; (II) the mean cell volume of the population of red blood cells calculated using impedance values; (III) the mean cellular hemoglobin concentration of the population, calculated using the mean cell volume, the bulk hemoglobin concentration, and the number of cells in the population; (IV) the mean values of the measurements of the population of red blood cells on the ALL and IAS channels; and (V) the median-of-means IAS value for prior populations of red blood cells analyzed on the IAS channel on the hematology analyzer.

In these embodiments, the ALL and IAS measurements may be scaled ALL and IAS measurements, i.e., ALL and IAS measurements that are adjusted relative to the initial ALL and IAS measurements prior to calculating the volume of the cell. In certain cases, the initial IAS measurement may be scaled to provide a scaled IAS value using: (I) the mean cellular hemoglobin concentration of the population of red blood cells, (II) the mean value of the measurements of the population of red blood cells on the IAS channel; and (III) the median-of-means IAS value obtained from prior samples run on the hematology analyzer. An exemplary formula for scaling the initial LAS measurement to provide a scaled IAS value is set forth in the Examples section of this disclosure. The initial ALL measurement may be scaled to provide a scaled ALL measurement using: (I) the scaled IAS value; (II) the mean cell volume of the population of red blood cells calculated using impedance values; and (III) the mean value of the measurements of the population of red blood cells in the ALL channel. An exemplary formula for scaling the initial ALL measurement to provide a scaled ALL measurement is set forth in the Examples section of this disclosure.

In certain embodiments and as described in greater detail in the Examples section of this disclosure, the hemoglobin content of individual red blood cells in the sample may be calculated using: (I) measurements of individual red blood cells on lAS and PSS channels; (II) the mean cellular hemoglobin concentration of the population (which is calculated using the mean cell volume based on impedance values, the bulk hemoglobin concentration, and the number of cells in the population); (III) the mean values of the measurements of the population of red blood cells on the IAS and PSS channels; and (IV) the median-of-means IAS and PSS values for prior populations of red blood cells analyzed on the IAS and PSS channels on the hematology analyzer.

In these embodiments, the IAS and PSS measurements may be scaled IAS and PSS measurements, i.e., IAS and PSS measurements that are adjusted relative to the initial IAS and PSS measurements prior to calculating the hemoglobin content of the cell. In certain cases, the initial IAS measurement may be scaled to provide a scaled IAS value using the method described above, i.e., by using: (I) the mean cellular hemoglobin concentration of the population of red blood cells, (II) the mean value of the measurements of the population of red blood cells on the IAS channel; and (III) the median-of-means IAS value obtained from prior samples run on the hematology analyzer. An exemplary formula for scaling the initial IAS measurement to provide a scaled IAS value is set forth in the Examples section of this disclosure. The initial PSS measurement may be scaled to provide a scaled PSS measurement using: (I) the mean cellular hemoglobin concentration of the population of red blood cells; (II) the mean value of the measurements of the population of red blood cells on the PSS channel; (III) the median-of-means PSS value obtained from prior samples run on the hematology analyzer. An exemplary formula for scaling the initial PSS measurement to provide a scaled PSS measurement is set forth in the Examples section of this disclosure.

In certain cases, in order to remove data points produced by noise (e.g., cell debris or other particles) and coincidences (i.e., unresolved movement of two cells across the light source of the hematology analyzer at very nearly the same time), the data points for whichever optical scattering channels are used may be filtered prior to use in the method, e.g., prior to any scaling that may occur. In some embodiments, the filtering removes high- and low-end measurements that are expected to result from noise and coincidences. In one embodiments, the data points for whichever channels are used (e.g., data for the ALL, IAS and/or PSS channels) are plotted on a histogram, and the boundaries of acceptable data can be set at defined percentages of the histogram peak height, as described in FIG. 3. For example, the boundaries of acceptable data can be set at a percentage in the range of 1% to 10%, e.g., 5%, of the histogram peak height. For removing coincidences and noise from IAS data for reticulocytes, the histogram bin used as upper boundary can be increased by 5% to 15%, e.g., 10% as compared to that used for the entire population of red blood cells, because the reticulocytes tend to be larger than the red blood cells, which means that data produced by coincidences tend to have higher values than for the entire population of red blood cells. Other methods are known for identifying and removing noise (at the lower range) and coincidences from optical data obtained from a hematology analyzer, and may be employed herein.

In some embodiments, the method may further comprise, as part of the calculating step, normalizing the measurements, e.g., after scaling the measurements. The normalization comprises adjusting the measurements relative to a constant so as to obtain quantities approximately 1, and further subtracting 1 so as to obtain normalized measurements distributed around 0. In particular embodiments, the initial data for each channel may be divided by a normalization constant (which is different for each channel), which constant may be empirically determined. The normalization constant may not change from sample to sample. Rather, it may be stable and not subject to change between samples unless a need arises.

As such, in particular embodiments, the method may include: a) obtaining a set of data points for a sample comprising a population of red blood cells using a hematology analyzer; b) removing data points corresponding to noise and coincidences to provide a filtered dataset; and c) calculating the volume or hemoglobin content of an individual red blood cell in the sample containing using: (I) measurements of individual red blood cells on a plurality of a optical scattering channels; (II) the mean cell volume of the population of red blood cells calculated using impedance values; (III) the bulk hemoglobin concentration of the sample; (IV) the number of cells in the population of red blood cells; (V) the mean values of the measurements of the population of red blood cells on the plurality of the optical scattering channels; and (VI) the median-of-means value of prior populations of red blood cells analyzed on at least one of the optical scattering channels on the hematology analyzer. The calculating includes scaling and normalizing the measurements, and inputting the so scaled, normalized measurements into a formula to obtain the volume and/or hemoglobin concentration of the cell.

Measurement of the volume of individual red blood cells and/or the amount of hemoglobin in individual red blood cells of a red blood cell population permits the analysis of further characteristics of the population. In one embodiment, the method may further comprise calculating the proportion (which may be expressed as a percentage, fraction or another number, for example), of red blood cells having a defined characteristic. For example, the method may be employed to calculate the proportion of red blood cells having a volume above and/or below a defined volume (e.g., the percentage of cells larger than 120 fL, i.e., the percentage of "macrocytic" red blood cells; or the percentage of cells smaller than 60 fL, i.e., the percentage of "microcytic" red blood cells). In another embodiment, the method may be employed to calculate the proportion of red blood cells having a hemoglobin concentration above and/or below a defined volume (e.g., the percentage of red blood cells having a cellular hemoglobin concentration of less then 28 g/dL, i.e., the percentage of "hypochromic" red blood cells; or the percentage of red blood cells having a cellular hemoglobin concentration of greater than 41 g/dL, i.e., the percentage of "hyperchromic" red blood cells). Likewise, the volumes and/or hemoglobin concentrations of individual red blood cells of a population may be statistically analyzed to identify other statistical measures that describe, e.g., the shape of the distribution or variation of the volume or hemoglobin concentration of individual RBCs within the population. In one exemplary embodiment, the width of the distribution of hemoglobin concentration in the population of red blood cells is calculated.

In a further embodiment, the method may further involve identifying reticulocytes, which are a subset of red blood cells that are distinguishable from other red blood cells by fluorescence, in the sample. The method may also be used to analyze the reticulocytes by, for example, calculating the mean amount of hemoglobin in the reticulocytes, the mean concentration of hemoglobin in the reticulocytes, or the mean volume of the reticulocytes, in a sample.

The hematology analyzer described above can be employed, for example, to investigate red blood cell disorders or anemias, and to make treatment decisions, if necessary. Examples of anemia include iron deficiency anemia, anemia of chronic disorder, and megaloblastic anemia caused by vitamin $B_{12}$ or folic acid. For example, administration of iron supplement is extremely effective as a treatment for iron deficiency anemia, but not for anemia of chronic disorder. The cause of the anemia is therefore important to the treatment of the anemia.

Iron deficiency is the most prevalent single deficiency state on a worldwide basis. It is important economically because it diminishes the capability of affected individuals to perform physical labor, and it diminishes both growth and learning in children.

Absolute iron deficiency, with anemia or without anemia, and functional iron deficiency are high-frequency clinical conditions, and these patients have iron-deficient erythropoiesis. Absolute iron deficiency is defined as a decrease in total iron body content. Iron deficiency anemia occurs when iron deficiency is sufficiently severe to diminish erythropoiesis and cause the development of anemia. Functional iron deficiency describes a state where the total iron content of the body is normal or even elevated, but the iron is "locked away" and unavailable for the production of red blood cells. This condition is observed mainly in patients with chronic renal failure who are on hemodialysis, and in patients with chronic inflammation or chronic infections.

Iron status can be measured using hematological and biochemical indices. Each parameter of iron status reflects changes in different body iron compartments and is affected at different levels of iron depletion. Specific iron measurements include hemoglobin, mean cell volume, hematocrit, erythrocyte protoporphyrin, plasma iron, transferrin, transferrin saturation levels, serum ferritin, soluble transferrin receptors and red-cell distribution width.

Hemoglobin has been used longer than any other iron status parameter. It provides a quantitative measure of the severity of iron deficiency once anemia has developed. Hemoglobin determination is a convenient and simple screening method and is especially useful when the prevalence of iron deficiency is high, as in pregnancy or infancy. The limitations of using hemoglobin as a measure of iron status are its lack of specificity (as factors such as vitamin $B_{12}$ or folate deficiency, genetic disorders and chronic infections can limit erythropoiesis) and its relative insensitivity due to the marked overlap in values between normal and iron deficient populations. To identify iron deficiency anemia, hemoglobin is measured together with more selective measurements of iron status.

A reduction in mean cell volume occurs when iron deficiency becomes severe, at about the same time as anemia starts to develop. It is a fairly specific indicator of iron deficiency once thalassemia and the anemia of chronic disease have been excluded. A cut-off value of 80 fl is accepted as the lower limit of the normal range in adults. The red-cell distribution width (RDW) has been used recently in combination with other parameters for the classification of anemias. It reflects the variation in the size of the red cells and can be used to detect subtle degrees of anisocytosis.

The most commonly used iron status parameters at present are transferrin saturation (TSAT) and serum ferritin. However, both are indirect measures of iron status. Transferrin is a transport protein that contains two iron binding sites by which it transports iron from storage sites to erythroid precursors. TSAT (i.e., the percentage of total binding sites that are occupied by iron) is a measure of iron that is available for erythropoiesis. TSAT is calculated by dividing the serum iron by the total iron binding capacity, a measurement of circulating transferrin, and multiplying by 100. Ferritin is a storage protein that is contained primarily within the reticuloendothelial system, with some amounts released in the serum. Under conditions of iron excess, ferritin production increases to offset the increase in plasma iron. The level of ferritin in the serum, therefore, reflects the amount of iron in storage.

Reticulocytes are immature red blood cells with a maturation time of only 1 to 2 days before turning into mature red blood cells. When these are first released from the bone marrow, measurement of their hemoglobin content can provide the amount of iron immediately available for erythropoiesis. A less-than-normal hemoglobin content in these reticulocytes is an indication of inadequate iron supply relative to demand. The amount of hemoglobin in these reticulocytes also corresponds to the amount of hemoglobin in mature red blood cells. The hemoglobin content of reticulocytes (CHr) has been evaluated recently in numerous studies as a test for iron deficiency and functional iron deficiency and has been found to be highly sensitive and specific. However, exact threshold values have not been established, as the threshold values vary depending on the laboratory and instrument used.

Erythropoietin is effective in stimulating production of red blood cells, but without an adequate iron supply to bind to hemoglobin, the red blood cells will be hypochromic, i.e., low in hemoglobin content. Thus, in states of iron deficiency, a significant percentage of red blood cells leaving the bone marrow will have a low hemoglobin content. By measuring the percentage of red blood cells with hemoglobin content less than 28 g/dL, iron deficiency can be detected. A percentage of hypochromic cells greater than 10% has been correlated with iron deficiency, and hence has been used as a diagnostic criterion for detection of iron deficiency.

Programming

In one embodiment, a physical memory containing instructions (i.e. "programming") for performing the method described above is provided. In some embodiments, the memory can comprise a physical computer-readable medium comprising programming to calculate: a) the volume of individual red blood cells of the sample using a method described above: and/or b) the amount of hemoglobin in individual red blood cells of the sample a the method described above.

In one embodiment, data from the hematology analyzer is collected, and programming containing an algorithm for the calculation is executed, using inputs from an FCS file.

The programming can be provided in a physical storage or transmission medium. A computer receiving the instructions can then execute the algorithm and/or process data obtained from the subject method. Examples of storage media that are computer-readable include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information can be "stored" on computer readable medium, where "storing" means recording information such that it is accessible and retrievable at a later date by a computer on a local or remote network.

The method described above can be automatically executed each time a sample is run.

EXAMPLES

Algorithm Implementation

Methods for measuring parameters of individual red blood cells (RBCs) are described herein. Certain parameters that can be measured include the fraction of RBCs smaller than 60 fL (percent microcytic, % Micro), the fraction larger than 120 fL (percent macrocytic, % Macro), the fraction of RBCs with a cellular HGB concentration of less than 28 g/dL (percent hypochromic, % Hypo) and those higher than 41 g/dL (percent hyperchromic, % Hyper). Other parameters of interest include the width of the distribution of HGB concentration in RBCs (Hemoglobin Distribution Width, HDW), the mean amount of HGB in reticulocytes (Mean Corpuscular Hemoglobin for Reticulocytes, MCHr), the mean concentration of HGB in reticulocytes (Mean Corpuscular Hemoglobin Concentration for Reticulocytes, MCHCr), the mean volume of reticulocytes (Mean Corpuscular Volume for Reticulocytes, MCVr), and the fraction of reticulated platelets (percent reticulated platelets, % rPLT).

The RBC parameters were derived from optical cell-by-cell scatter data in ALL, IAS and PSS using optical cellular hemoglobin concentration (CHC) and optical volume models. The following examples describe in detail the implementation of these models.

Data Event Filtering

Figure 2:
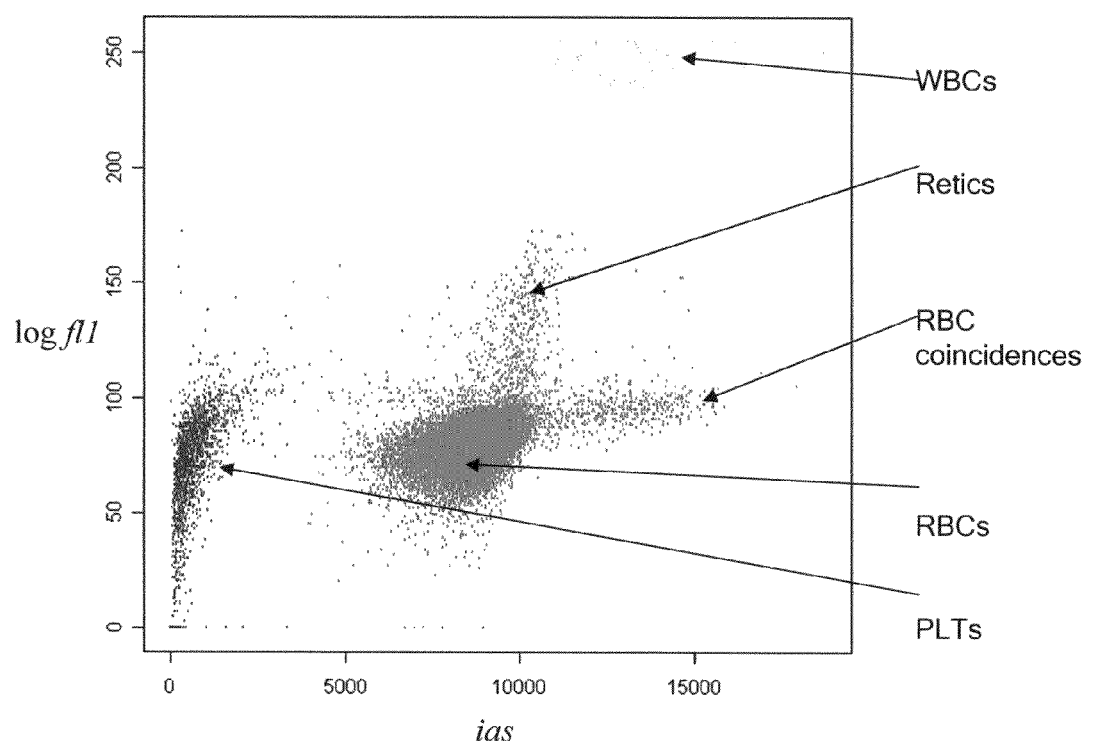
FIG. 2 is a plot of blood cells collected in the reticulocyte assay on a CELL-DYN Sapphire hematology analyzer from Abbot Diagnostics.

A Retic assay (which comprises collecting RBC, PLT, and Retic cellular events, as well as some WBC cellular events) was performed and ALL, IAS, PSS, and FL1 data were collected. The RBC algorithms described below used data from all of these sources. FIG. 2 illustrates the log FL1 vs. linear IAS forms of the data from the Retic assay.

Figure 3:
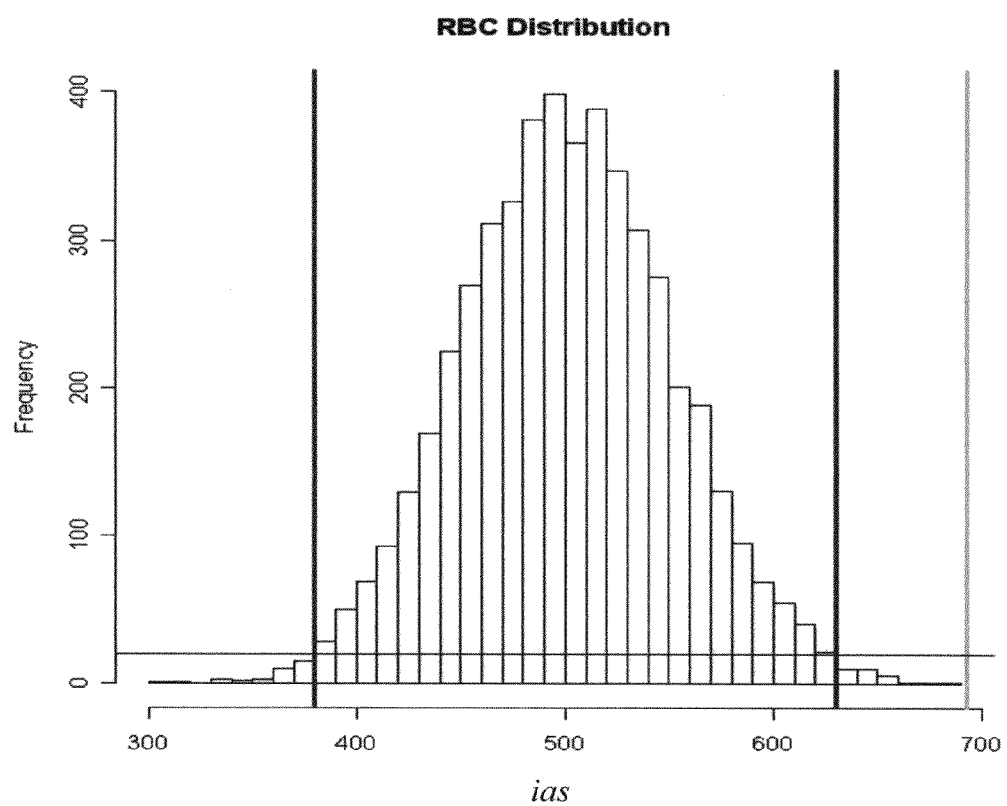
FIG. 3 is a graph showing exemplary thresholds applied to a red blood cell (RBC)/reticulocyte (Retic) distribution.

The Retic assay separates RBCs (red blood cells) and Retics (reticulocytes) from PLTs (platelets) and WBCs (white blood cells). The same classifications were used for the present example, but with a closer examination of the RBCs and Retics. As shown in FIG. 2, the RBCs presented a certain amount of coincidences (quantified around a few percent of the total RBC count), which should be eliminated before any calculations. Therefore, the highest point of the distributions of the population of RBCs and Retics was found in the three relevant detection channels (ALL, IAS and PSS), and then the boundaries of acceptable data were set at 5% of the histogram peak height. These thresholds served to eliminate noise (at the low end) and coincidence events (at the high end), and were derived from the data in a prior study. For removing coincidences and noise in the Retics, the top level IAS boundary previously derived was increased by 10% because the Retics tend to be larger than the RBCs. FIG. 3 shows the thresholds used to gate the RBCs and Retics. The horizontal line above the x axis is the 5% level relative to the maximum. The internal vertical lines are the RBC thresholds, which are placed at the first bins outside the 5% threshold. In this example, the lower thresholds for both RBCs and Retics were at channel 380. The upper RBC threshold was at channel 630. Adding 10%, channel 693 was obtained, which was used as the upper threshold for the Retics (vertical line on right).

Models and Channel Scaling Schemes

Figure 4:
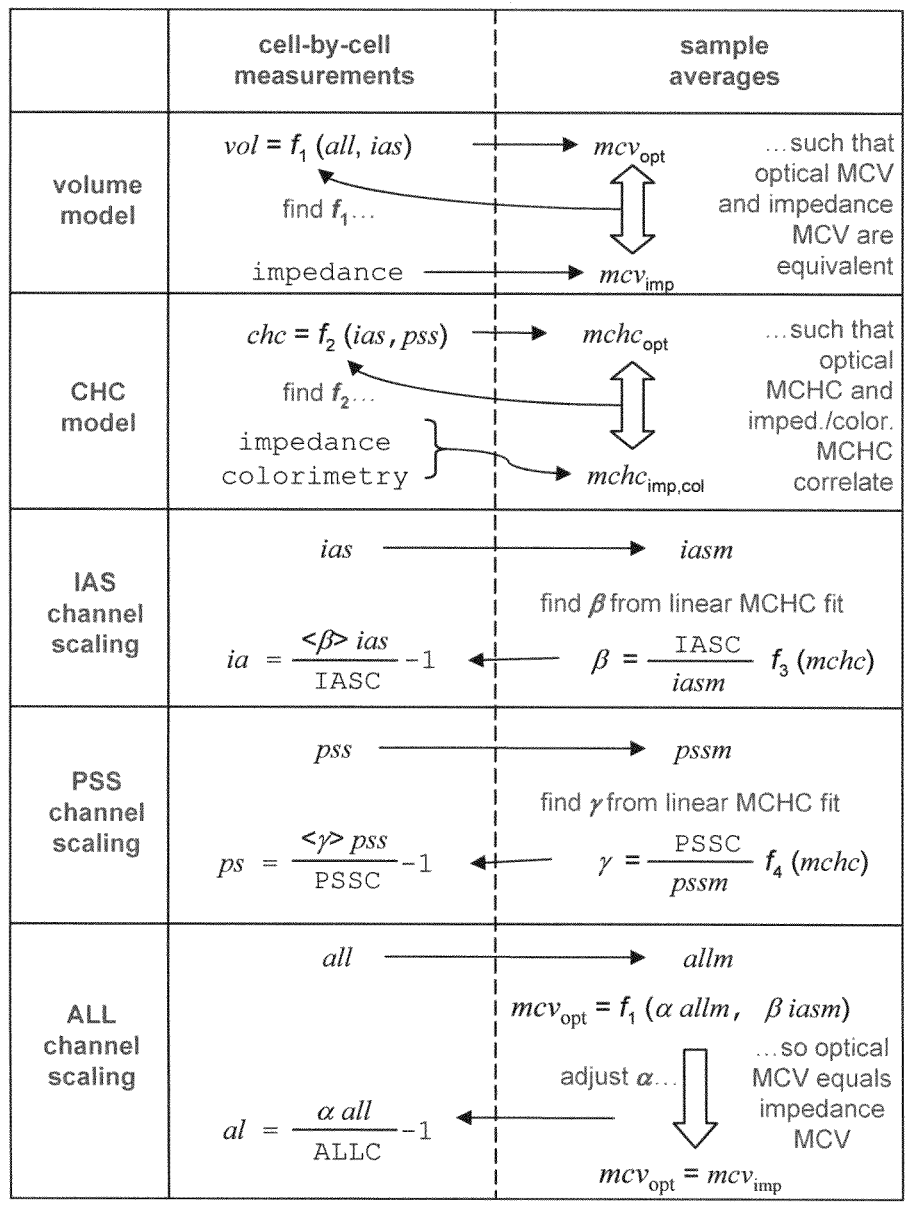
FIG. 4 is a table that maps the relationships in the volume and cellular concentration models.

The way the channels were scaled is closely linked to the way the volume and CHC models were constructed. FIG. 4 maps those relationships.

Referring to FIG. 4, there were variables, as well as functions, that were built from and apply to sets of individual cell-by-cell measurements (left column); and other variables and functions that were related to means of such sets (right column).

The quantities in the table of FIG. 4 are defined and discussed in the following passage. After applying the filtering boundaries as described in "Data Event Filtering" above, the mean values (in IAS, ALL and PSS) of the remaining RBCs and Retics were determined. These mean values were used to build the volume and CHC models, and were used to calibrate the channel scaling factors.

Since RBC parameters can be used on analyzers with different gain settings, the algorithm contains a mechanism to normalize and to scale the measurements from IAS, PSS, and ALL before they were used in the calculations. The optical normalization and scaling (on a cell-by-cell basis) was as follows:

$$al = \left(\frac{\alpha \, all}{ALLC}\right) - 1$$

$$ia = \left(\frac{median(\beta)ias}{IASC}\right) - 1$$

$$ps = \left(\frac{median(\gamma)pss}{PSSC}\right) - 1$$

Here al, ia, and ps are the scaled and normalized scatter values and all, ias, and pss are the measured values of each cell on the respective detection channels ALL, IAS, and PSS. The measured values were first normalized by the constants ALLC, IASC, and PSSC, respectively. After normalization, they were multiplied by their respective channel scaling factor ($\alpha$, $\beta$, and $\gamma$, respectively; for IAS and PSS the value used is a median from a history log, described below). The resulting value should be approximately 1. Then 1 is subtracted to have values that are distributed around 0 for a normal event.

The values of the normalization constants were ALLC=13235.25, IASC=6041.75, and PSSC=11500; these values were derived from a training set of data, which was archived, and are not subject to change for analyzers with the same hardware and firmware configuration; they simply normalize the values to around 1.

The channel scaling factors, on the other hand (which are of order unity), were used to compensate for slight inter-analyzer differences and intra-analyzer drifts in optical performance. The analyzer kept a running log of the samples run on it; for IAS and PSS, the algorithm used the latest 51 valid samples to compute the channel scaling factor medians used above, while for ALL, the channel scaling factor was computed newly for each sample (based on impedance MCV data), without reference to old samples. See "Standardization" below on how the scaling factors were derived and managed.

Because the RBC parameters were calculated from absolute channel values, it may be important to track the optical calibration of the instrument. The optically derived parameters were adjusted based on the reported impedance MCV and colorimetric HGB results. The adjustment was implemented by changing channel scaling factors on a sample-by-sample basis.

The IAS and PSS channel scaling factors, β and γ, were calculated from the impedance and colorimetric MCHC measurements, $mchc_{imp,col}$:

$$mchc_{imp,col} = \frac{hgb_{col}}{rbc_{imp} * mcv_{imp}}$$

where $hgb_{col}$ is the numerical value of HGB concentration from the colorimetric transducer, $rbc_{imp}$ indicates the concentration of RBCs in the sample obtained from impedance data, and $mcv_{imp}$ is the mean RBC volume from impedance data. Since MCHC exhibits a lower reproducibility and lower repeatability than other parameters (as, e.g., MCV), a simple linear relation was used to tie the IAS and PSS values to MCHC. The equations that were used on a sample-by-sample basis were:

$$\beta = IASC\left(\frac{48.5 - mchc_{imp,col}}{13.9 \, iasm}\right)$$

$$\gamma = PSSC\left(\frac{mchc_{imp,col} - 25.4}{7.1 \, pssm}\right)$$

The numerical constants in the above equations follow from a first order linear fit to data collected on four CELL-DYN Sapphires™ during the Feasibility Study. The iasm and pssm variables are the mean IAS and PSS values, respectively, for all RBCs in any particular sample. The IASC and PSSC constants were used as above to normalize the iasm and pssm variables so that the scaling factors were around unity.

The ALL channel scaling factor, α, was calculated from the measured impedance MCV, the scaled mean IAS value and the ALL measurement. The equations were derived from the optical volume model (see "Volume Model" below):

$$\alpha = \frac{\sqrt{b^2 - 4ac} - b}{2a}$$

where
a=327.41 allnorm²
b=(213.51−605.78 iam−2*327.41)allnorm
c=84.02−213.51+(605.78−125.32)iam +260.64 iam²+ 327.41 allnorm−mcv$_{imp}$
and $$iam = \left(\frac{\beta \, iasm}{IASC}\right) - 1$$

$$allnorm = \frac{allm}{ALLC}$$

where iasm and allm are the sample means of all the cell-by-cell IAS and ALL measurements, respectively, and $mcv_{imp}$ is the impedance MCV value.

Essentially, these formulae take the quadratic volume model dependent on mean ALL (allm) and IAS (iasm); insert the IAS scaling obtained through the MCHC linear fit above (β); constrain the volume result to equal the impedance value ($mcv_{imp}$); and solve for the ALL scaling factor required to satisfy the equation (α). Since the ALL channel scaling factor is tied to the impedance MCV, which exhibits good reproducibility and good repeatability, there is no need to take a median of the last 51 samples.

Volume Model

Figure 5:
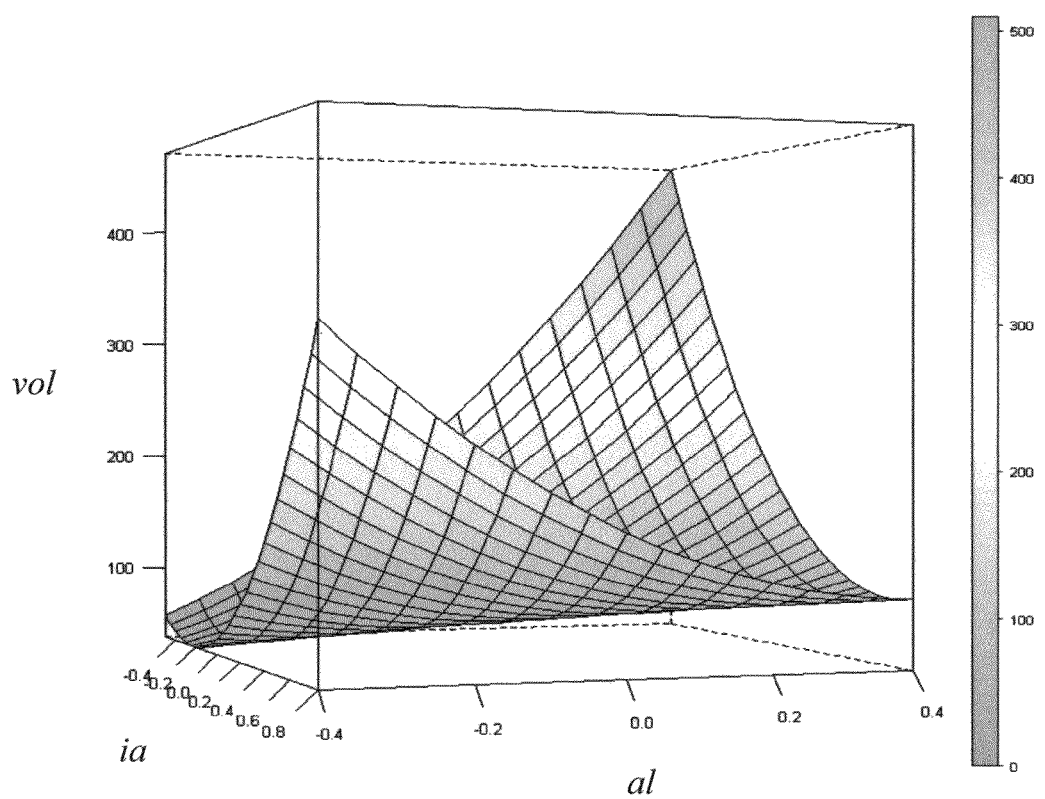
FIG. 5 is a graphical representation of the model used to calculate cell volume.
Figure 6:
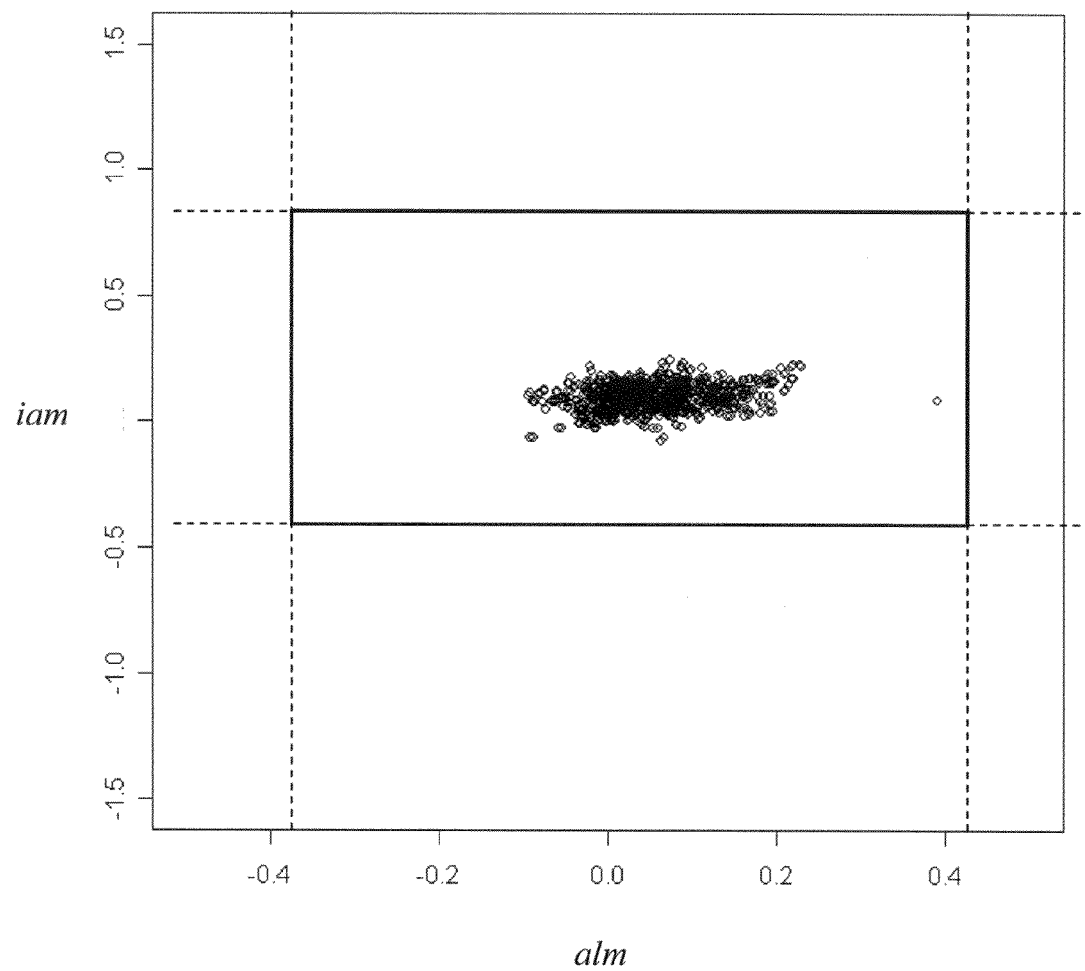
FIG. 6 is a plot showing the data points from a study, representing the mean scaled and normalized axial light loss and intermediate angle scattering values of all the cells of a particular sample. Data points were used to create the model used to calculate cell volume. The internal lines show the extent of the volume model surface.

The volume model is based on the measurement of each cell in IAS and ALL. The formula used to calculate the volume vol (on a cell-by-cell basis) is as follows:

vol=84.02−125.32  ia+213.51  al−605.78
ia*al +260.64 ia²+327.41 al² where ia and al are the cell-by-cell scaled measurements defined in "Models and Channel Scaling Schemes" above. The coefficients in this second-order global model (meaning an analytical model that applies to all the cells in the sample) were derived from the earlier study. To get the correct volume, the channel scaling factors for IAS and ALL were known (see equations in "Models and Channel Scaling Schemes" above). FIG. 5 shows a graphical representation of the volume model. FIG. 6 shows the 977 data points from a study plotted on the iam vs. alm (means of ia and al, respectively) plane. Each data point represents the mean al and ia of all the cells of that particular sample; the various points comprise the entire set of samples from the study. The rectangle around the data points shows the extent in parameters for which the surface was calculated. The areas with the least data coverage lie along the iam boundaries. It is noted that the optical volume model was not used to determine % Micro and % Macro (which were extracted from the impedance MCV data), but only as a basis to calculate MCVr and MCHr and to plot individual RBCs in a chc-vol scattergram.

Local CHC Model

The cell-by-cell optical CHC model is based on the measurement of each cell in IAS and PSS. The model is based on a local fit. In order to implement the local model in the code, the model was sampled on a regular grid. The grid of numbers was imported into the software of the hematology analyzer used. The software finds all 4 nearest grid points, and does a linear interpolation between those 4 points.

The axes of the grid were normalized IAS and PSS measurements. The cell-by-cell IAS and PSS measurements were normalized and scaled as described already in "*Models and Channel Scaling Schemes*" above and reported below:

$$ia = \left(\frac{median(\beta)ias}{IASC}\right) - 1$$

$$ps = \left(\frac{median(\gamma)pss}{PSSC}\right) - 1$$

The IAS and PSS channel scaling factors β and γ, which are applied to all cells in the sample under test, were calculated using the median of the scaling factors obtained for the latest 51 samples. The model values at the grid points are shown in FIG. 7.

If the ia and ps values were outside of the range for which the CHC model was defined, the closest edge value of the model was used. This was supported by the analysis presented below.

Figure 7:
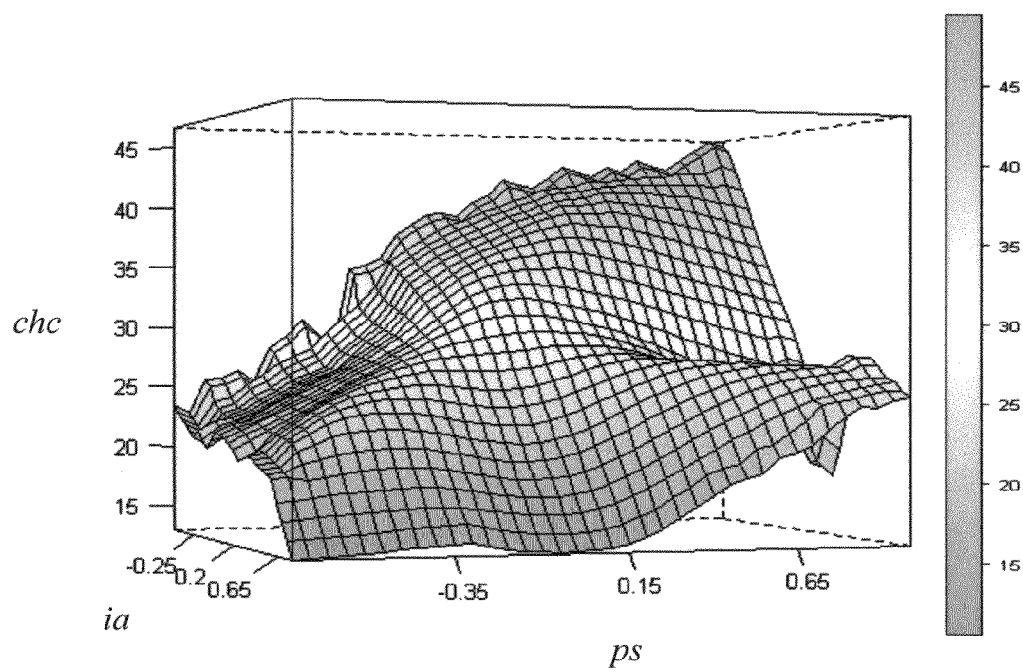
FIG. 7 is a graphical representation of the local model used to calculate cellular hemoglobin concentration (the CHC local model).
Figure 8:
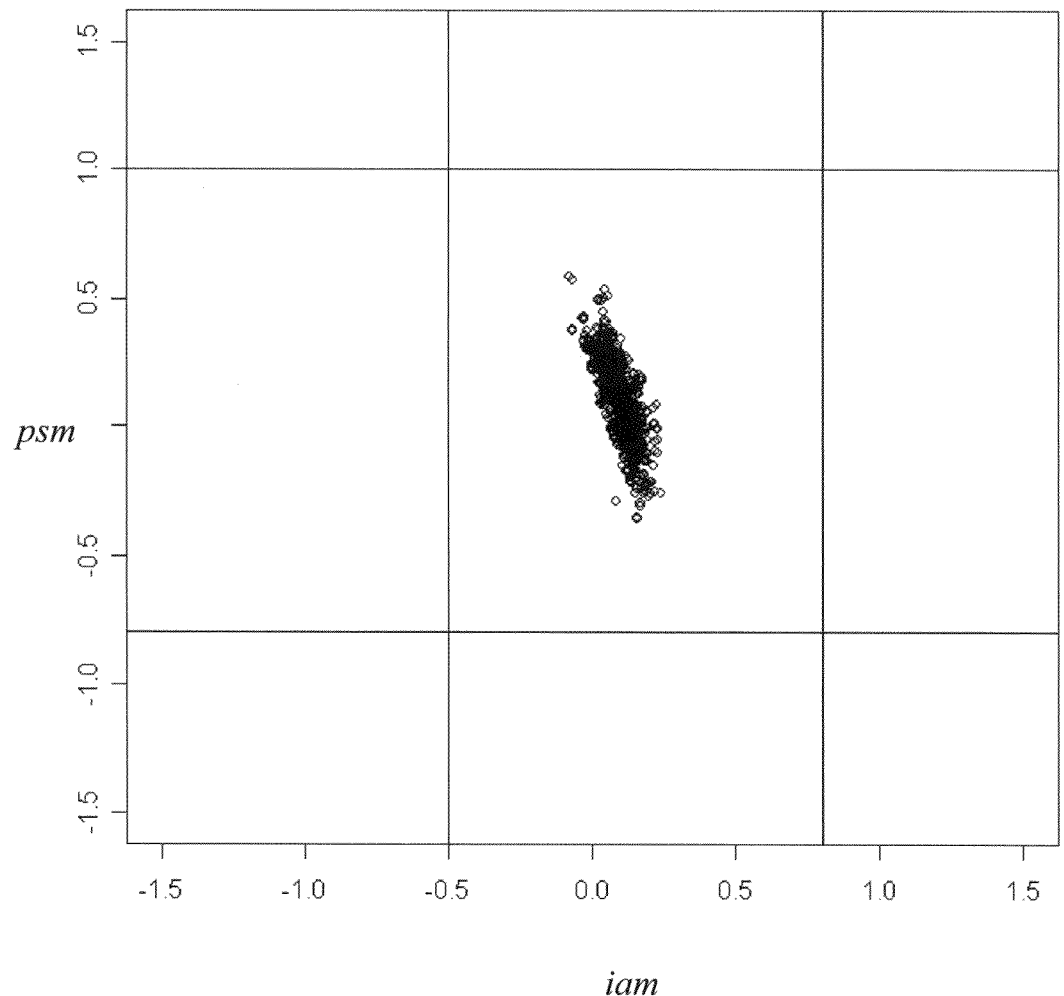
FIG. 8 is a plot showing the data points used to create the CHC local model. The internal lines show the extension of the CHC model surface.

FIG. 8 shows the 977 data points, from the same study used in the volume model, which were used to derive the surface model of FIG. 7, plotted on the psm vs. iam (mean of ps and ia, respectively). As in FIG. 6, each data point represents the mean ps and ia of all the cells of that particular sample; the various points comprise the entire set of samples from the study. The rectangle around the data points shows the extent in parameters for which the surface has been calculated. The areas with the least data coverage lie along the iam boundaries.

Figure 9:
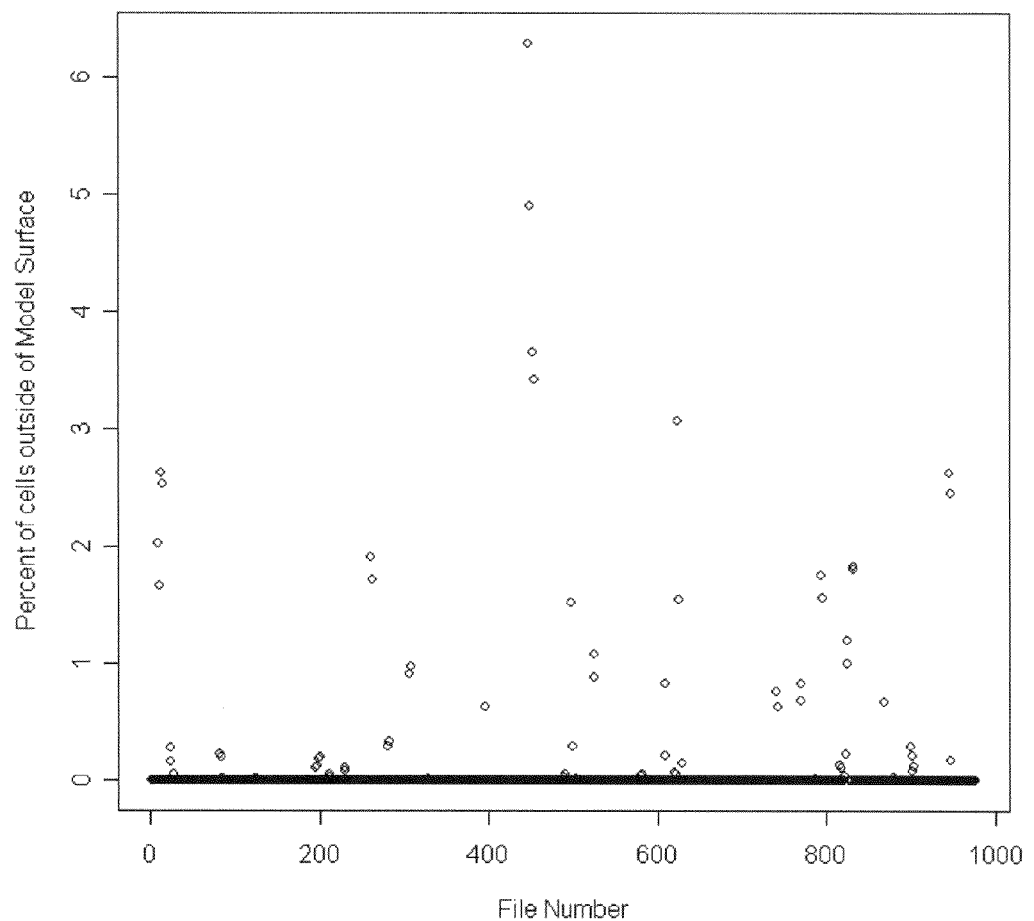
FIG. 9 is a plot of the percentages of RBC/Retic points that fall outside the CHC model surface for 977 samples in a study.
Figure 10:
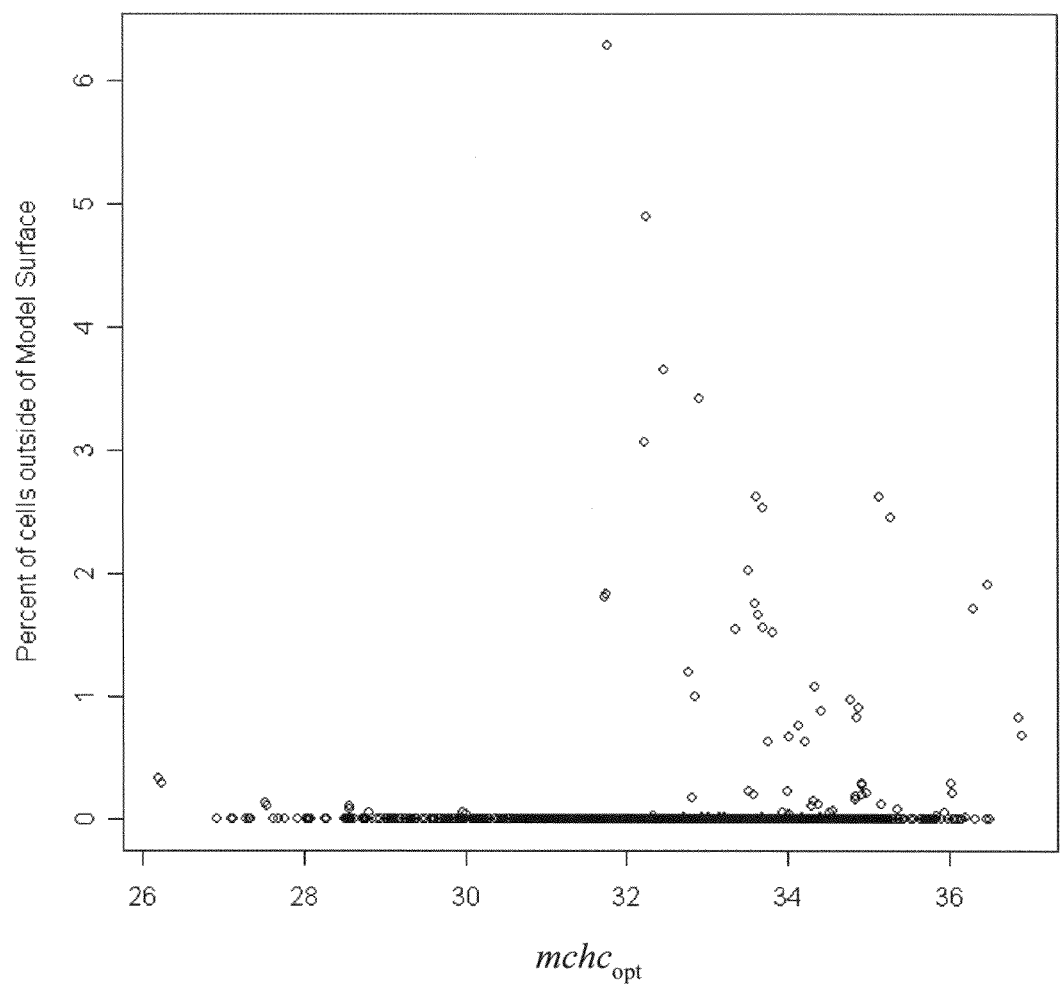
FIG. 10 is a plot of the percentages of RBC/Retic points that fall outside of the CHC model surface for the 977 samples from a study as a function of optical MCHC values.

FIG. 9 shows a graph with the percentage of cells falling outside of the model boundaries for each of the 977 samples from the study. The maximum was around 6%. FIG. 10 shows the same results plotted against the optically derived MCHC value of the sample.

Figure 11:
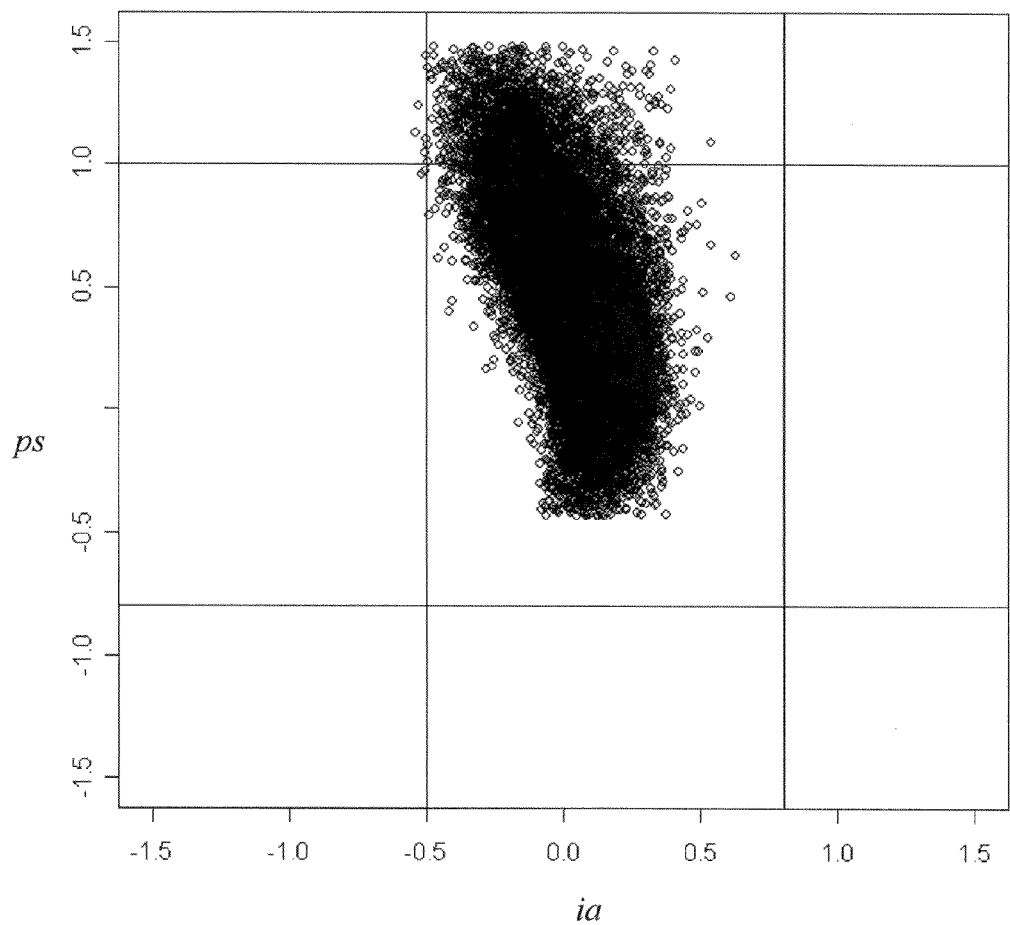
FIG. 11 is a plot of all RBC/Retic events in the plane of scaled, normalized intermediate angle and polarized side scattering for the sample in the study with the most events (6%) outside of the CHC model surface.
Figure 12:
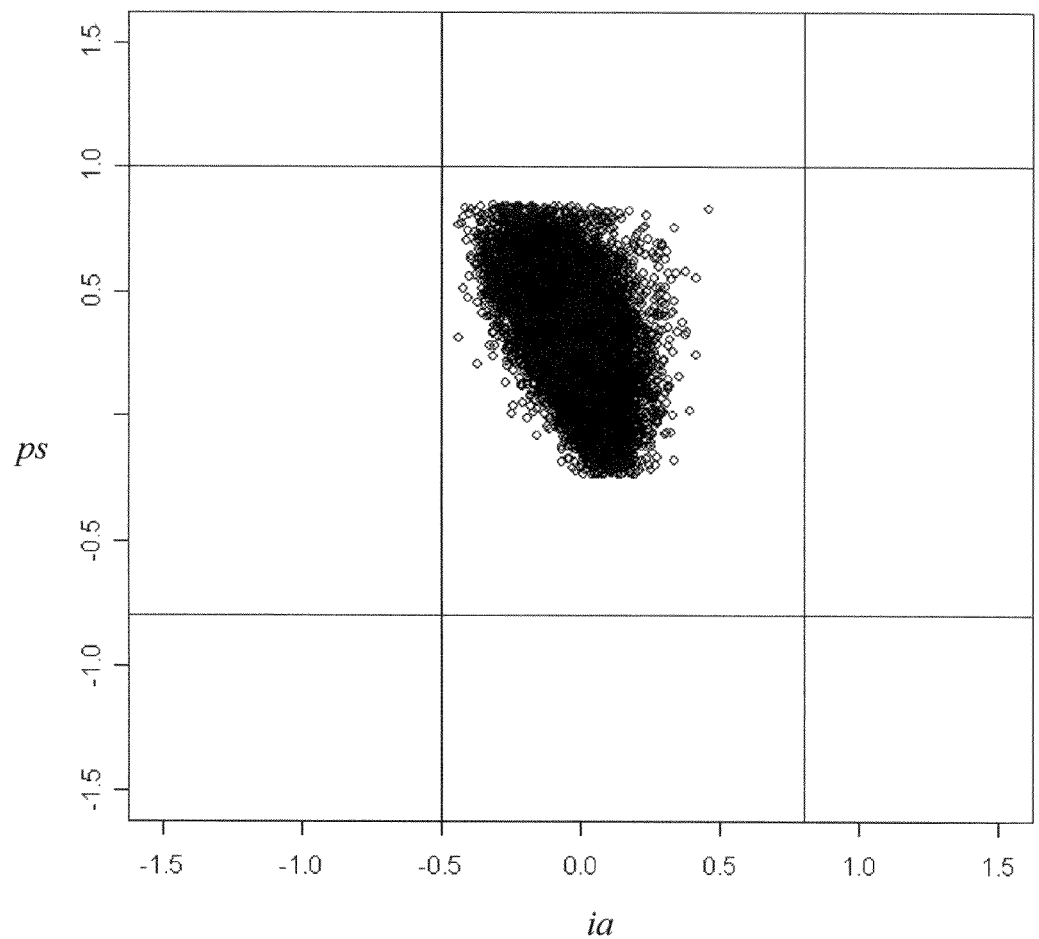
FIG. 12 is a plot of all RBC/Retic events in the of scaled, normalized intermediate angle and polarized side scattering plane for another sample in the study with an MCHC of 32 g/dL.

FIG. 11 is a ps vs. ia plot (i.e., a plot, for a single sample, of the scaled and normalized values of PSS and IAS of all the individual cells in the sample; contrast with the plots in FIGS. 6 and 8, which plot sample means) for the sample with 6% of events outside of the model boundary. This particular sample had a much broader PSS distribution than was usually observed. For comparison, FIG. 12 shows the distribution pattern for a typical sample with an MCHC value of about 32 g/dL.

Those relatively few events (in those relatively very few samples) that were outside of the model surface were mostly leaving the surface on the high-ps boundary. Looking at the shape of the model surface in FIG. 7, the gradient in ps along the high-ps boundary of the surface was generally small (compared to the overall CHC variation across the entire model surface). Based on these results, it was acceptable to use the values of the model on the high-ps boundary for those events that extend beyond it. This approach, further generalized to the other boundaries, was implemented in the algorithm.

Calculated Parameters

With optical cell-by-cell models for CHC and volume for each RBC and Retic event, the desired parameters can be calculated.

HDW: The robust standard deviation (rSD) of the CHC distribution was calculated for all Retics and RBCs. The rSD was calculated as rSD=1.4826 median($chc$−median($chc$))

The factor of 1.4826 ensured that for normally distributed data the rSD and the normal SD were identical. The HDW was given as a percentage by dividing the rSD by the median and multiplying by 100.

% Hypo, % Hyper: All RBCs and Retics were counted with chc<28 g/dl (% Hypo) and chc>41 g/dl (% Hyper). The count was divided by the total number of RBCs and Retics and multiplied by 100.

MCHCr: Only the CHC values (chc) of the Retics were used and their mean calculated.

MCVr: Only the volume (vol) of the Retics was used and their mean calculated.

MCHr: The product of chc and vol for each Retic were determined, their mean calculated and divided by 100.

% Micro and % Macro

The % Micro and % Macro parameters were measured from the impedance histogram. The % Micro was the fraction of RBCs that were smaller than 60 fL. The % Macro was the fraction of RBCs that were larger than 120 fL. RBC coincidences were removed and the numbers of the cells above (% Macro) and below (% Micro) the limits were summed up, respectively.

Removing the coincidences was important for samples which had a low number of % Macro events. The impedance count typically had 3% coincidences, which were recorded at a volume of roughly twice the MCV value. So for an MCV of 80 fL, it was expected to see 3% of the RBC events as coincidences around a volume of 160 fL. In order to give a good estimate of the % Macro, those 3% coincidences should be eliminated because they would otherwise be counted as macrocytic. The algorithm looked for a valley in the volume histogram and limited the valid RBC events to those to the left (i.e., with volumes smaller than that) of the bottom of the valley. Accordingly, coincidence events were generally correctly excluded from the calculation of macrocytic RBCs.

Reticulated Platelets

Also provided is a method of enumerating reticulated platelets (rPLT). In general terms, the method relies on the same principle used for the reticulated RBC assay, whereby a suitable cell-permeable nucleic-acid dye or nucleic-acid stain binds to the RNA in the reticulocytes and makes them distinguishable from mature RBCs, in which RNA is absent. Reticulated PLTs also present a nonzero RNA content, which sets them apart from mature PLTs. The nucleic-acid dye or stain confers to reticulated PLTs similar signal-differentiation characteristics as it does to reticulated RBCs; for example, in the case of a fluorescent-conjugated cell-permeable nucleic-acid dye, reticulated RBCs typically exhibit higher fluorescence than mature RBCs, and reticulated PLTs typically exhibit higher fluorescence than mature PLTs. This elevation of fluorescence can be exploited by suitably designed algorithms.

Figure 13:
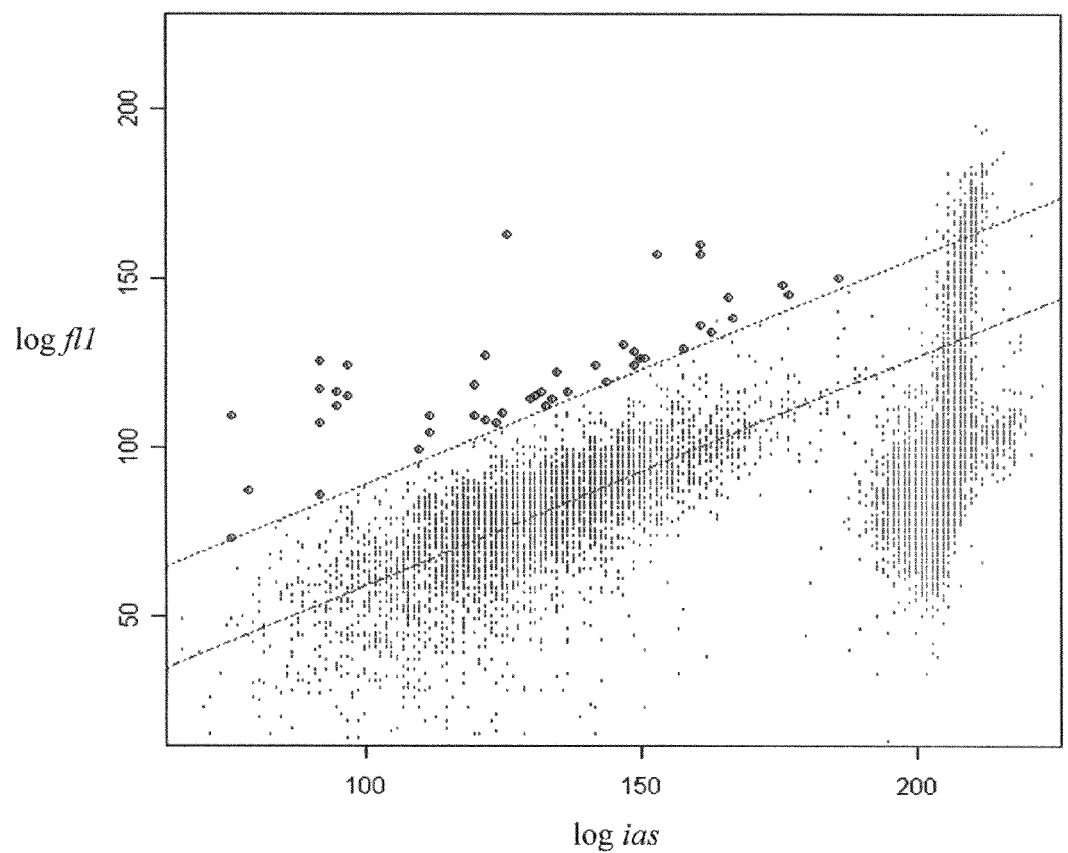
FIG. 13 schematically depicts the algorithm used for classifying reticulated platelets (rPLT) in a normal sample. rPLTs are the circled events.

An algorithm with the best straight-line fit through the platelet population (in log fl1 vs. log ias) was used. Another line with the same slope and a positive offset of 30 channels was drawn. The number 30 was previously determined using a training set so that a set of normal samples had an average % rPLT of about 2%, which is typical in healthy subjects. Any platelet event that was above the second line was classified as a reticulated PLT. FIG. 13 illustrates the algorithm for classifying rPLTs in a normal sample. The platelets are shown in blue, and the dash-dotted line through the population is the best-fit line. The dashed line is the line offset by 30 and all rPLT events above it are circled. In this particular sample the rPLT percentage was 1.0%.

In case there were less than 150 platelets in the FCS file, a default slope of 0.5 was used, which was only fit for the offset of the line through the platelet population.

Standardization

The gain settings for ALL and PSS in the Retic assay were set according to the following procedure.

The gains for the WBC differential assay were first standardized. A value of 20V was subtracted from the PSS PMT voltage setting for the WBC differential assay. The resulting value was used as the PSS PMT voltage setting for the Retic assay (e.g.: V_PMT$_{PSS,WBC/diff}$=387V; V_PMT$_{PSS,Retic}$=387V−20V=367V). The PSS amplifier gain settings were copied from the WBC differential assay to the Retic assay.

The ALL pre-amplifier gain setting for the WBC differential assay was multiplied by 2, and used as the ALL pre-amplifier gain setting for the Retic assay (e.g.: preampgain$_{ALL,WBC/diff}$=16; preampgain$_{ALL,Retic}$=32). The ALL amplifier gain setting was copied from the WBC differential assay to the Retic assay.

After the voltages and gains were set, 3.3-μm standard reference particles (SRPs) at a concentration of 250×10⁶/mL were used to establish the initial channel scaling factors. The SRPs were run in the Retic RBC Reference SRP mode.

The algorithm used the means of the SRPs in the ALL, IAS and PSS detection channels to obtain the initial channel scaling factors. The initial channel scaling factors were calculated as $$\alpha = \frac{4893}{\text{mean}(all_{SRP})}$$

$$\beta = \frac{2328}{\text{mean}(ias_{SRP})}$$

$$\gamma = \frac{31311}{\text{mean}(pss_{SRP})}$$

where α, β, and γ, the channel scaling factors, again represent the ALL, IAS, and PSS channel scaling factors, respectively. The mean channels here were represented at full resolution (15 bit). The initial scaling factors were stored in a configuration file. For each sample, a new determination of the scaling factors was obtained, following the procedure detailed in "Models and Channel Scaling Schemes" above. The 51 most recent estimates of the scaling factors were stored in the configuration file.

Deconvolution with Instrument Profile

From the impedance transducer, a measurement of $RDW_{imp}$ (the width of the RBC volume distribution histogram) was obtained and compared with the optically-derived $RDW_{opt}$ from the cell-by-cell scattering measurements to get an estimate of how much instrument-dependent degradation there might be in the optical RDW measurement.

An empirical model was constructed relating the ratio of $RDW_{opt}/RDW_{imp}$ to the instrument profiles in ALL and IAS. The model allowed the deconvolution of the optical degradation out of the IAS and ALL signals.

The implemented model assumed the instrument profile as well as the sample profile to be Gaussian. Under this assumption the deconvolution was performed by reducing the IAS and ALL distributions widths around their respective means. Each was multiplied by the ratio of the desired to existing total distribution width.

The instrument distribution width was estimated by the ratio of the measured optical distribution width of the RBC volumes to the impedance distribution width (RDW).

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto.

What is claimed is:

1. A method for calculating a volume, a hemoglobin content, or both, of a red blood cell in a blood sample, the method comprising:
   passing a blood sample through a flow cell of a hematology analyzer;
   directing light to the flow cell from a light source;
   generating optical data using one or more optical detectors for detecting optical characteristics of the blood sample;
   measuring a hemoglobin concentration in the blood sample using a colorimetric transducer;
   measuring a change in impedance in the blood sample using an impedance transducer; and
   calculating a volume, a hemoglobin content, or both, of a red blood cell in the blood sample based on the optical data, the hemoglobin concentration, and the change in impedance.

2. The method of claim 1, wherein the one or more optical detectors is selected from the group consisting of: an axial light loss (ALL) detector, an intermediate angle scatter (IAS) detector, a depolarized side scatter (DSS) detector, a polarized side scatter (PSS) detector, a green fluorescence (FL1) detector, a yellow to orange fluorescence (FL2) detector, a red fluorescence (FL3) detector, and any combination thereof.

3. The method of claim 1, wherein the one or more optical detectors comprises an axial light loss (ALL) detector and an intermediate angle scatter (IAS) detector.

4. The method of claim 1, wherein the one or more optical detectors comprises a polarized side scatter (PSS) detector and an intermediate angle scatter (IAS) detector.

5. The method of claim 1, comprising calculating a volume of the red blood cell.

6. The method of claim 5, wherein the volume of the red blood cell is calculated using a second order global volume model that comprises an ALL measurement and an IAS measurement of the red blood cell.

7. The method of claim 1, comprising calculating a hemoglobin content of the red blood cell.

8. The method of claim 7, wherein the hemoglobin content of the red blood cell is calculated using a local fit cellular hemoglobin concentration model that comprises a PSS measurement and an IAS measurement of the red blood cell.

9. The method of claim 1, comprising calculating a volume and a hemoglobin content of the red blood cell.

10. The method of claim 1, further comprising scaling the optical data, filtering the optical data, normalizing the optical data, standardizing the optical data the optical data, or any combination thereof.

11. The method of claim 1, wherein filtering the optical data comprises removing data that corresponds to noise, data that corresponds to coincidence events, or both.

12. The method of claim 1, further comprising calculating an amount of red blood cells in the blood sample that have a volume that is greater than or less than a defined value.

13. The method of claim 12, wherein the defined value is from 60 fL to 120 fL.

14. The method of claim 13, wherein the defined value is 80 fL.

15. The method of claim 1, further comprising calculating an amount of red blood cells in the blood sample that have a hemoglobin concentration that is greater than or less than a defined value.

16. The method of claim 15, wherein the defined value is from 28 g/dL to 41 g/dL.

17. The method of claim 1, further comprising determining a distribution of the volumes of a population of red blood cells in the blood sample.

18. The method of claim 1, further comprising determining a distribution of the concentration of hemoglobin in a population of red blood cells in the blood sample.

19. The method of claim 1, further comprising:
   determining a number of reticulocytes in the blood sample; and analyzing the mean amount of hemoglobin in the reticulocytes, the mean concentration of hemoglobin in the reticulocytes, the mean volume of the reticulocytes, or any combination thereof.

20. The method of claim 1, further comprising deconvoluting an optical degradation value from the optical data obtained from the one or more detectors.

* * * * *